(12) United States Patent
Simpson et al.

(10) Patent No.: US 10,363,069 B2
(45) Date of Patent: Jul. 30, 2019

(54) SPINAL CORRECTION CONSTRUCT AND METHOD

(71) Applicant: Warsaw Orthopedic, Inc., Warsaw, IN (US)

(72) Inventors: Joshua W. Simpson, Collierville, TN (US); William Alan Rezach, Covington, TN (US); Richard Quinn Brown, Collierville, TN (US); Rodney R. Ballard, Lakeland, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 158 days.

(21) Appl. No.: 15/222,721

(22) Filed: Jul. 28, 2016

(65) Prior Publication Data
US 2018/0028234 A1    Feb. 1, 2018

(51) Int. Cl.
*A61B 17/70* (2006.01)
*A61B 17/56* (2006.01)
*A61B 17/68* (2006.01)
*A61B 90/00* (2016.01)
*A61B 17/00* (2006.01)

(52) U.S. Cl.
CPC ...... *A61B 17/7017* (2013.01); *A61B 17/7014* (2013.01); *A61B 17/7025* (2013.01); *A61B 17/7037* (2013.01); *A61B 2017/00991* (2013.01); *A61B 2017/00995* (2013.01); *A61B 2017/567* (2013.01); *A61B 2017/681* (2013.01); *A61B 2090/064* (2016.02)

(58) Field of Classification Search
CPC ............ A61B 17/7014; A61B 17/7025; A61B 17/7016; A61B 17/7017
See application file for complete search history.

(56) References Cited

U.S. PATENT DOCUMENTS

| | | | |
|---|---|---|---|
| 9,301,784 B2 | 4/2016 | Zhao et al. | |
| 2009/0076597 A1* | 3/2009 | Dahlgren | A61B 17/7016 623/2.1 |
| 2014/0296918 A1* | 10/2014 | Fening | A61B 17/7016 606/258 |

\* cited by examiner

*Primary Examiner* — Julianna N Harvey
(74) *Attorney, Agent, or Firm* — William Richter

(57) ABSTRACT

A spinal construct includes at least one body including a first biasing member engageable with a longitudinal element for translation thereof relative to the body in a first direction. A second biasing member is engageable with a lock. The lock is connected with the longitudinal element to resist and/or prevent translation of the longitudinal element relative to the body in a second direction. Implants, surgical instruments, systems and methods are disclosed.

18 Claims, 10 Drawing Sheets

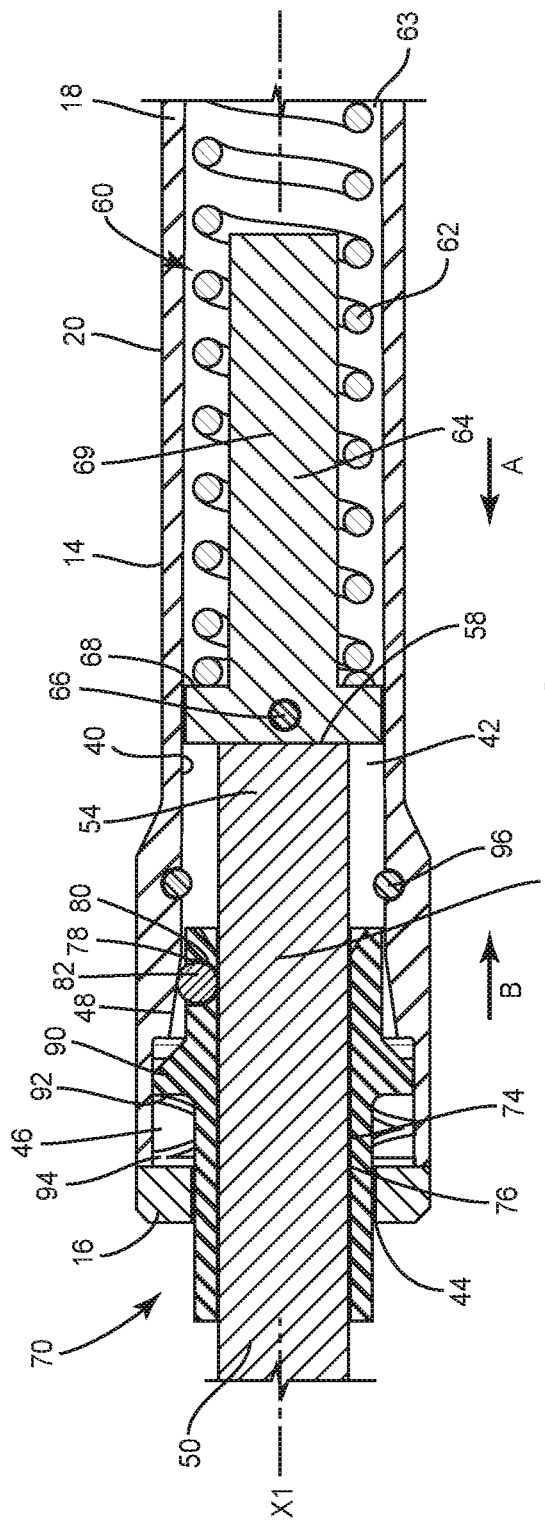
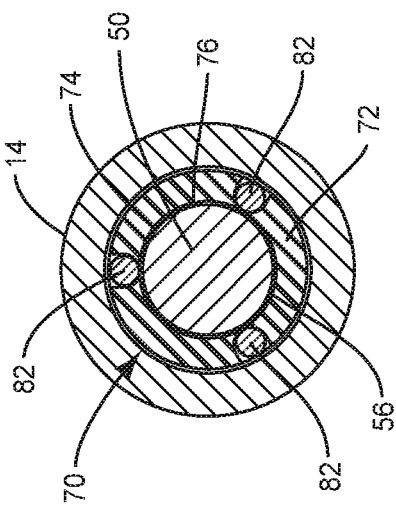
FIG. 2
FIG. 3

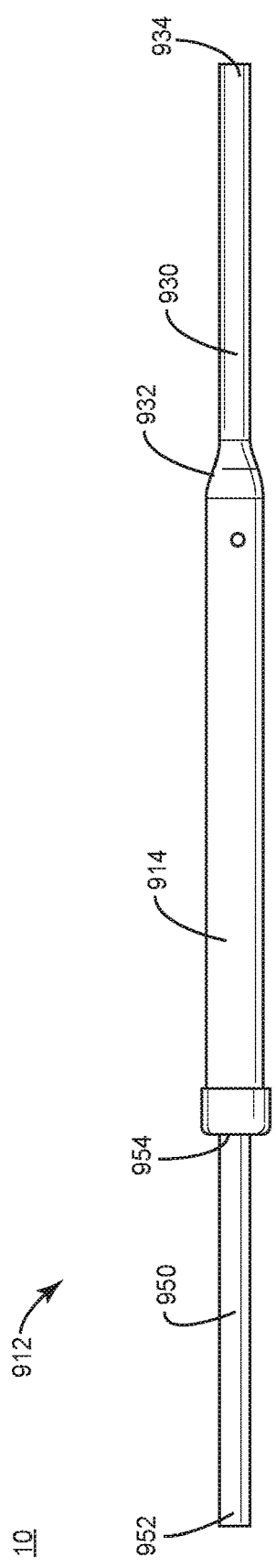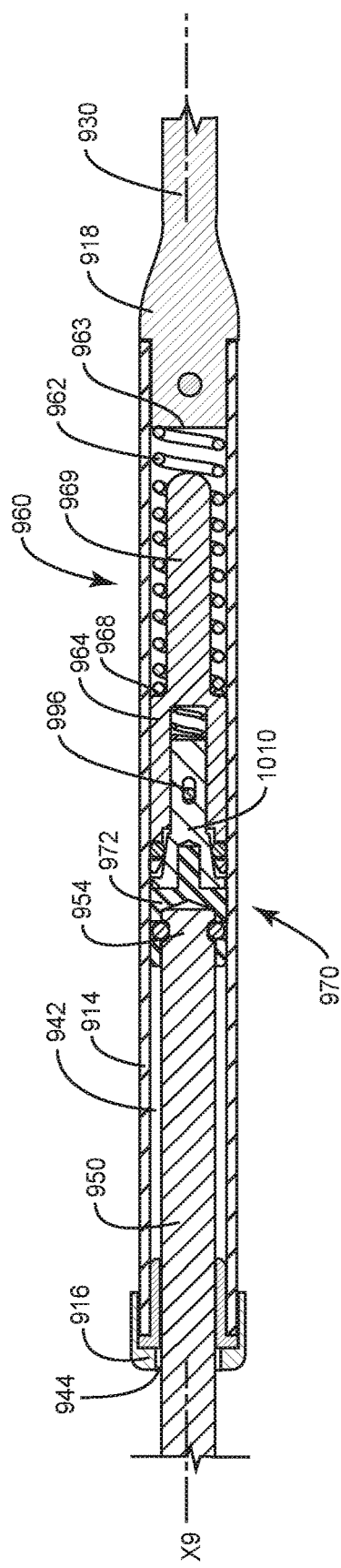

SPINAL CORRECTION CONSTRUCT AND METHOD

TECHNICAL FIELD

The present disclosure generally relates to medical devices for the treatment of musculoskeletal disorders, and more particularly to a surgical system and a method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degeneration caused by developmental conditions, injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants such as rods, tethers and bone screws for stabilization of a treated section of a spine. This disclosure describes an improvement over these prior technologies.

SUMMARY

In one embodiment, a spinal construct is provided. The spinal construct includes at least one body including a first biasing member engageable with a longitudinal element for translation thereof relative to the body in a first direction. A second biasing member is engageable with a lock. The lock is connected with the longitudinal element to resist and/or prevent translation of the longitudinal element relative to the body in a second direction. In some embodiments, implants, surgical instruments, systems and methods are disclosed.

In one embodiment, a method for treating a spinal disorder is provided. The method includes the steps of: disposing an expandable spinal construct in a selected configuration; fixing the spinal construct in the selected configuration with a member; attaching a first end of the spinal construct with tissue; attaching a second end of the spinal construct with tissue; and disengaging the member from the spinal construct to release the spinal construct from the selected configuration.

In one embodiment, the method includes the steps of: attaching a first end of a spinal construct with tissue, the spinal construct including a plurality of bodies, each body including a biasing member engageable with a longitudinal element for translation relative to the body to expand the spinal construct; and attaching a second end of the spinal construct with tissue and disposing the plurality of bodies in a selected orientation with tissue to create at least one zone of treatment with the tissue.

BRIEF DESCRIPTION OF THE DRAWINGS

The present disclosure will become more readily apparent from the specific description accompanied by the following drawings, in which:

FIG. 2 is a cross section view of the components shown in FIG. 1;

FIG. 3 is an end view of the components shown in FIG. 1;

FIG. 14 is a side view of components of one embodiment of a surgical system in accordance with the principles of the present disclosure;

FIG. 15 is a cross section view of the components shown in FIG. 14; and

DETAILED DESCRIPTION

Figure 1:
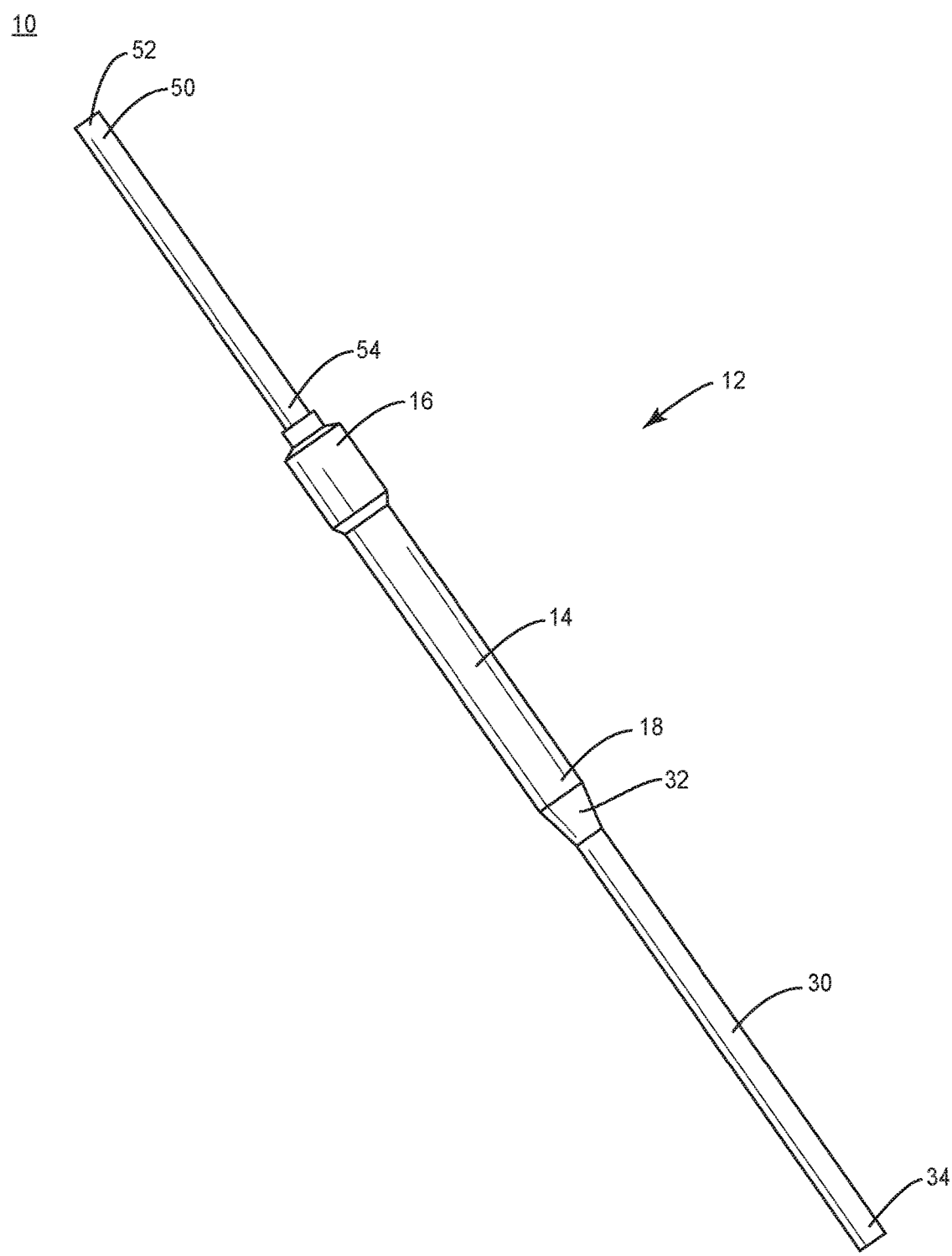
FIG. 1 is a perspective view of components of one embodiment of a surgical system in accordance with the principles of the present disclosure.

The exemplary embodiments of the system and related methods of use disclosed are discussed in terms of medical devices for the treatment of musculoskeletal disorders and more particularly, in terms of a surgical system and method for treatment of a spine disorder. In some embodiment, the present system and method can be employed to treat scoliosis in a growing child and utilize a spinal construct, which may include, for example, growing rods, vertical expandable prosthetic titanium ribs, Shilla technique components, vertebral body stapling and/or tethers. In some embodiments, the present system and method can include limitations based on type and magnitude of spinal deformity effectively treated, age of a patient, and underlying co-morbidities, which may impact outcome.

In some embodiments, the surgical system includes a spinal construct having a self-distracting rod. In some embodiments, the surgical system is configured to distract the spine without fusion to prevent progression of a spinal curvature while allowing a thoracic capacity of a child to develop. In some embodiments, the self-distracting rod is configured to resist and/or prevent a need for surgeries every six months. In some embodiments, the surgical system is inexpensive, simple and avoids manipulated distraction.

In some embodiments, the surgical system includes a self-distracting rod having a lock with a tapered crimp configuration. In some embodiments, the surgical system includes a self-distracting rod having a biasing member, such as, for example, a follower and a spring configured to maintain a load on the rod by removing slack in the spinal construct.

In some embodiments, the surgical system includes a self-distracting rod that is configured to prevent forcing correction of the spine and provides for natural growth. In some embodiments, the surgical system is configured to facilitate screw placement and correction of the spine. In some embodiments, the surgical system includes a self-distracting rod having bearings configured to translate along a taper of a lock. In some embodiments, translation along the taper causes the bearings to apply a force to the rod to prevent the rod from backing up while allowing the rod to extend and/or expand the spinal construct and the spine to grow.

In some embodiments, the spinal construct includes a follower spring configured to apply a force against the rod. In some embodiments, the surgical system includes a self-distracting rod configured to facilitate growth while maintaining a load on the spine without repeated surgeries or doctor visits. In some embodiments, the surgical system includes a self-distracting rod having a locking mechanism configured to facilitate and guide growth while the follower spring applies pressure combining both growth guidance and distraction.

In some embodiments, the surgical system includes a self-distracting rod including for example, ball bearings, a body, an extending rod and a biasing member having a lock mechanism. In some embodiments, the surgical system includes a self-distracting rod having a follower spring configured to apply a pressure to the rod to generate force.

In some embodiments, the force that pushes on the extending rod is generated by a constant pressure. In some embodiments, the surgical system includes a self-distracting rod having a high pressure chamber and a low pressure chamber with a one-way valve disposed therebetween. In some embodiments, a constant pressure is maintained in the lower pressure chamber as the volume changes thereby causing a constant force on the rod.

In some embodiments, the surgical system includes a spinal construct having one or more self-distracting rods configured to provide concurrent extension. In some embodiments, the surgical system includes a spinal construct having at least two self-distracting rods configured for disposal in sequence to increase an extended length, increase force, and allow for rod contouring between the two rod mechanisms. In some embodiments, the spinal construct includes at least two self-distracting rods each having a different spring force. In some embodiments, the differing forces of the self-distracting rods facilitate distraction of a thoracic spine at a different rate than a lumbar spine to resist and/or prevent kyphosis of the spine. In some embodiments, the spinal construct includes a body having at least two self-distracting rods and the body can be made of different materials to change the stiffness of the construct. In some embodiments, the spinal construct includes a first self-distracting rod having a flexible configuration relative to a second self-distracting rod.

In some embodiments, the surgical system includes a self-distracting rod configured to provide opposed distraction. In some embodiments, the surgical system includes at least two self-distracting rods being fixed to an apex of the spine to correct an apex curvature, while allowing and guiding growth and maintaining a constant force on the spine. In some embodiments, the surgical system includes a self-distracting rod to facilitate derotation.

In some embodiments, the surgical system includes a self-distracting rod having a release mechanism. In some embodiments, the release mechanism is configured to facilitate delivery of the self-distracting rod to an operating room in a compressed and/or non-extended configuration such that the rod can be activated to grow without putting an unexpected load on the spine.

In some embodiments, the surgical system is configured for assembly in a compressed orientation and a coupling member, such as, for example, a set screw is engaged with the rod to hold the rod in place. In some embodiments, the set screw is released intra-operatively, slowly in a controlled manner so that no unexpected forces are placed onto the spine. In some embodiments, the surgical system includes a rod that is configured to threadingly engage a body to resist and/or prevent extension of the rod from the body until insertion at a surgical site.

In some embodiments, the surgical system includes a lock that is configured to facilitate extension of the spinal construct while resisting and/or preventing restriction of the spinal construct. In some embodiments, the lock can disengage to allow for growth. In some embodiments, the surgical system includes a mechanism that applies a force to an extending rod to maintain a constant force on the spine by following the growth of the spine. In some embodiments, the surgical system includes an intra-operative release mechanism to initiate extension of the rod in a safe and controlled manner. In some embodiments, the surgical system provides for flexibility of placement to be used in distraction techniques, growth guidance techniques, or combinations of the two techniques. In some embodiments, the surgical system may include force sensors configured to measure a force on the spine and provide feedback to the surgeon. In some embodiments, the surgical system includes a release mechanism that is configured to resorb at precise time periods to initiate a subsequent phase of growth. In some embodiments, the surgical system includes rods having a low friction and/or low wear material to eliminate wear debris.

In some embodiments, the surgical system includes a spinal construct that distracts the spine without fusion to prevent progression of a spinal curve while allowing a thoracic capacity of the child to develop. In some embodiments, the surgical system avoids the need for surgeries every six months to adjust the spinal construct. In some embodiments, the spinal construct includes a body having three bearings configured to translate along a taper of a lock that collapses on the rod and resists and/or prevents the rod from backing up, while allowing the rod to grow. In some embodiments, the spinal construct includes a follower and a spring configured to apply a force to the rod. In some embodiments, the spinal construct is configured to allow growth, but maintain a load on the spine without repeated surgeries or doctor visits.

In some embodiments, one or all of the components of the present surgical system may be disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, vessels, ligaments, tendons, cartilage and/or bone unless specifically referred to otherwise.

The following discussion includes a description of a surgical system including spinal constructs, implants, surgical instruments, related components and methods of employing the system in accordance with the principles of the present disclosure. Alternate embodiments are disclosed. Reference is made in detail to the exemplary embodiments of the present disclosure, which are illustrated in the accompanying figures. Turning to FIGS. 1-3, there are illustrated components of a surgical system, such as, for example, a spinal correction system 10.

The components of spinal correction system 10 can be fabricated from biologically acceptable materials suitable for medical applications, including metals, synthetic polymers, ceramics and bone material and/or their composites. For example, the components of spinal correction system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal correction system 10 may have material composites, including the above materials, to achieve various desired characteristics such as strength, rigidity, elasticity, compliance, biomechanical performance, durability and radiolucency or imaging preference. The components of spinal correction system 10, individually or collectively, may also be fabricated from a heterogeneous material such as a combination of two or more of the above-described materials. The components of spinal correction system 10 may be monolithically formed, integrally connected or include fastening elements and/or instruments, as described herein.

Spinal correction system 10 is employed, for example, with an open or mini-open, minimal access and/or minimally invasive including percutaneous surgical technique and includes one or more spinal constructs for a correction treatment at a surgical site within a body of a patient, for example, a section of a spine to treat various spine pathologies, such as, for example, adolescent idiopathic scoliosis and Scheuermann's kyphosis. In some embodiments, the components of spinal correction system 10 are configured to deliver and introduce components of a spinal construct 12 that includes implants, such as, for example, one or more spinal rods, bodies, sleeves, connectors and/or fasteners. Spinal construct 12 forms one or more components of a correction treatment and/or correction system 10 implanted with tissue for positioning and alignment to stabilize a treated section of vertebrae.

Spinal construct 12 includes a body having a sleeve 14. Sleeve 14 defines a longitudinal axis X1. Sleeve 14 extends between an end 16 and an end 18. In some embodiments, sleeve 14 has a tubular cross section. In some embodiments, sleeve 14 may have an oval, oblong, triangular, square, rectangular, polygonal, irregular, uniform, non-uniform, offset, staggered, undulating, arcuate, variable and/or tapered configuration. Sleeve 14 includes an outer surface 20.

The body of spinal construct 12 includes a rod 30 extending from end 18. Rod 30 extends between an end 32 and an end 34. In some embodiments, end 32 is monolithically formed with sleeve 14. In some embodiments, rod 30 is integrally connected or includes fastening elements for connection with sleeve 14. In some embodiments, outer surface 20 tapers between end 18 and rod 30 such that rod 30 includes a smaller dimension, such as, for example, a diameter or thickness, than sleeve 14. In some embodiments, sleeve 14 and/or rod 30 may have a uniform thickness/diameter. In some embodiments, sleeve 14 and/or rod 30 may have various surface configurations, such as, for example, rough, threaded for connection with surgical instruments, arcuate, undulating, dimpled, polished and/or textured. In some embodiments, a dimension defined by sleeve 14 and/or rod 30 may be uniformly increasing or decreasing, or have alternate dimensions along its length. In some embodiments, sleeve 14 and/or rod 30 may have various lengths. End 34 is configured for engagement with tissue and/or a spinal implant, such as, for example, a bone fastener, as described herein.

Sleeve 14 includes an inner surface 40 that defines a cavity, such as, for example, a passageway 42. Passageway 42 extends axially within sleeve 14. In some embodiments, passageway 42 may extend within sleeve 14 at alternate orientations, relative to sleeve 14, such as, for example, arcuate, transverse, perpendicular and/or other angular orientations such as acute or obtuse, coaxial and/or may be offset or staggered.

Passageway 42 includes an opening 44 adjacent end 16. Passageway 42 and opening 44 are configured for movable disposal of a longitudinal element, such as, for example, a spinal rod 50, as described herein. Rod 50 is configured to translate within passageway 42 relative to sleeve 14, as described herein. In some embodiments, rod 50 is configured for dynamic axial translation relative to sleeve 14, as described herein. Passageway 42 has a circular cross section. Surface 40 defines a cavity 46 for disposal of a portion of a lock 70, as described herein, and a tapered portion 48 for engagement with lock 70. In some embodiments, tapered portion 48 may include a constant taper throughout a length. In some embodiments, tapered portion 48 extends along a discrete length of sleeve 14. In some embodiments, tapered portion 48 includes a substantially continuous slope, or may include different slopes along the length.

In some embodiments, passageway 42 may have alternate cross section configurations for disposal of alternately shaped spinal rods, such as, for example, oval, oblong, triangular, square, polygonal, irregular, uniform, non-uniform, offset, undulating, arcuate, variable and/or tapered. In some embodiments, inner surface 40 may define cross section configurations, such as, for example, mating, engaging and/or different from the cross section of one or more spinal rods disposed within passageway 42 such that sleeve 14 may limit, resist and/or prevent rotational movement of the one or more spinal rods relative to sleeve 14.

Rod 50 extends between an end 52 and an end 54. Rod 50 includes a surface 56 engageable with an inner surface of lock 70 to facilitate translation of rod 50 relative to sleeve 14 in a first direction and to resist and/or prevent translation of rod 50 in a second direction, as described herein. In some embodiments, rod 50 includes a smaller dimension, such as, for example, a diameter or thickness, than sleeve 14. In some embodiments, rod 50 may have a uniform thickness/diameter. In some embodiments, rod 50 may have various surface configurations, such as, for example, rough, threaded for connection with surgical instruments, arcuate, undulating, dimpled, polished and/or textured. In some embodiments, rod 50 may be equivalent to the size of rod 30. In some embodiments, rod 50 may be a different size, such as, for example, having a different diameter than rod 30. In some embodiments, rod 50 may be an alternate material than rod 30. In some embodiments, a dimension defined by rod 50 may be uniformly increasing or decreasing, or have alternate dimensions along its length. In some embodiments, rod 50 may have various lengths. End 52 is configured for engagement with tissue and/or a spinal implant, such as, for example, a bone fastener, as described herein.

End 54 is configured for disposal within passageway 42. End 54 includes a surface 58 configured for connection with a biasing member 60, as shown in FIG. 2. Biasing member 60 includes a coil spring 62 and a follower 64. Follower 64 is configured for moveable disposal within sleeve 14 and driven or urged in a selected direction under the bias force of spring 62 to facilitate translation of rod 50, as described herein. In some embodiments, such translation of rod 50 includes expansion of spinal construct 12 under the bias force of spring 62 to provide a constant pressure to rod 50 for growth guidance and distraction. In some embodiments, follower 64 includes a T-shaped cross section. In some embodiments, follower 64 comprises a piston. In some embodiments, the biasing member may include an elastomeric member, clip, leaf spring, gravity induced configuration, pneumatic configuration, hydraulic configuration and/or manual lever. In some embodiments, follower 64 is connected with end 54 by a pin 66. In some embodiments, follower 64 is monolithically formed with end 54. In some embodiments, follower 64 is integrally connected or includes fastening elements for connection with end 54.

Spring 62 is disposed within sleeve 14 and extends between a surface 63 of sleeve 14 and a surface 68 of follower 64. In some embodiments, surface 63 is fixed and surface 68 is moveable relative to sleeve 14. In some embodiments, spring 62 extends about an extension 69 of follower 64. Spring 62 applies a force and/or load to surface 68 causing follower 64 to drive and/or urge rod 50 in a direction, as shown by arrow A in FIG. 2. As such, rod 50 is urged to expand spinal construct 12 under a constant force of spring 62. In some embodiments, spring 62 facilitates dynamic translation of rod 50 during growth. Dynamic translation of rod 50 allows spinal construct 12 to respond to an active and/or changing spine. For example, as forces and/or force changes are applied to spinal construct 12, such as, for example, patient growth, trauma and degeneration, and/or system 10 component creep, deformation, damage and degeneration, one or more components of spinal construct 12, for example, sleeve 14, rod 50 and biasing member 60 adapt and/or are continuously adjustable with a responsive force to maintain the applied force transmitted from the bone fasteners substantially constant.

In some embodiments, the dynamic biasing force of spring 62 facilitates a self-distracting spinal construct 12. Translation of rod 50 allows spinal construct 12 to selectively adjust its length to accommodate growth to avoid multiple surgeries. In some embodiments, spinal construct 12 includes one or more components, as described herein, disposed in a selected orientation, as described herein, to guide growth along a selected path, while maintaining a load on the spine.

Rod 50 is engageable with lock 70. Lock 70 includes a sleeve 72. Sleeve 72 includes an inner surface 74 that defines a cavity, such as, for example, a passageway 76. Rod 50 extends through passageway 76. Sleeve 72 includes a surface 78 that defines three openings 80 disposed in a spaced apart relation about sleeve 72. Openings 80 are equidistantly and circumferentially disposed about sleeve 72 for communication with passageway 76. In some embodiments, surface 78 defines one or a plurality of openings 80.

Openings 80 are configured for disposal of bearings 82. Bearings 82 are configured to roll and/or slide between surface 56 and tapered portion 48 to facilitate translation of rod 50 relative to sleeve 14 in a direction, as shown by arrow A in FIG. 2, and/or expansion of the components of spinal construct 12. In some embodiments, rod 50 is translatable relative to sleeve 14 and/or the components of spinal construct 12 are expandable in a non-locking orientation of spinal construct 12.

Upon translation of rod 50 relative to sleeve 14 in a direction, as shown by arrows B in FIG. 2 and/or compression/contraction of the components of spinal construct 12, bearings 82 slide/roll into a more narrow space between surfaces 56, 48 for an interference and/or frictional engagement therewith to compress and/or crimp rod 50 with tapered portion 48 to resist and/or prevent translation of rod 50 relative to sleeve 14 in a direction, as shown by arrows B in FIG. 2 and/or compression/contraction of the components of spinal construct 12, as described herein. In some embodiments, translation of rod 50 relative to sleeve 14 and/or compression/contraction of the components of spinal construct 12 is resisted and/or prevented in a locked orientation of spinal construct 12. In some embodiments, lock 70 is disengageable or removable from a locked orientation. In some embodiments, lock 70 is fixed in a locked orientation. In some embodiments, biasing member 60 and lock 70 are engageable with rod 50 and comprise a strut to resist and/or prevent compression/contraction of the components of spinal construct 12 in a direction, as shown by arrows B in FIG. 2.

Lock 70 includes a flange 90 circumferentially disposed about sleeve 72. Flange 90 includes a surface 92. Cavity 44 is configured for disposal of a portion of lock 70, which includes a biasing member, such as, for example, a wave spring 94, as shown in FIG. 2. In some embodiments, the biasing member of lock 70 may include an elastomeric member, clip, coil spring, leaf spring, gravity induced configuration, pneumatic configuration, hydraulic configuration and/or manual lever.

Spring 94 applies a force and/or load to surface 92 to drive and/or urge lock 70 in a direction, as shown by arrow B in FIG. 2, stabilizing motion and/or positioning of lock 70 with passageway 42. In some embodiments, spring 94 drives and/or urges lock 70 to a locked orientation of spinal construct 12. In some embodiments, a stop element, such as for example, a ring 96 is disposed with sleeve 14 to enhance locking and/or facilitate disposal in a locked orientation of spinal construct 12. In some embodiments, lock 70 includes a range of movement and ring 96 comprises a limit to facilitate limitation of translation of rod 50 in a direction, as shown by arrow B in FIG. 2.

In some embodiments, spinal construct 12 prevents axial migration of rod 50 while maintaining a dynamically movable configuration of rod 50. In some embodiments, rod 50 may include a dynamically axially translatable configuration, as described herein, and spinal construct 12 may be configured, as described herein, such that spinal construct 12 may limit, resist and/or prevent movement in at least one direction of rod 50 relative to sleeve 14. Translation of bearings 82 along taper portion 46 facilitates locking and unlocking of lock 70 relative to rod 50.

Figure 4:
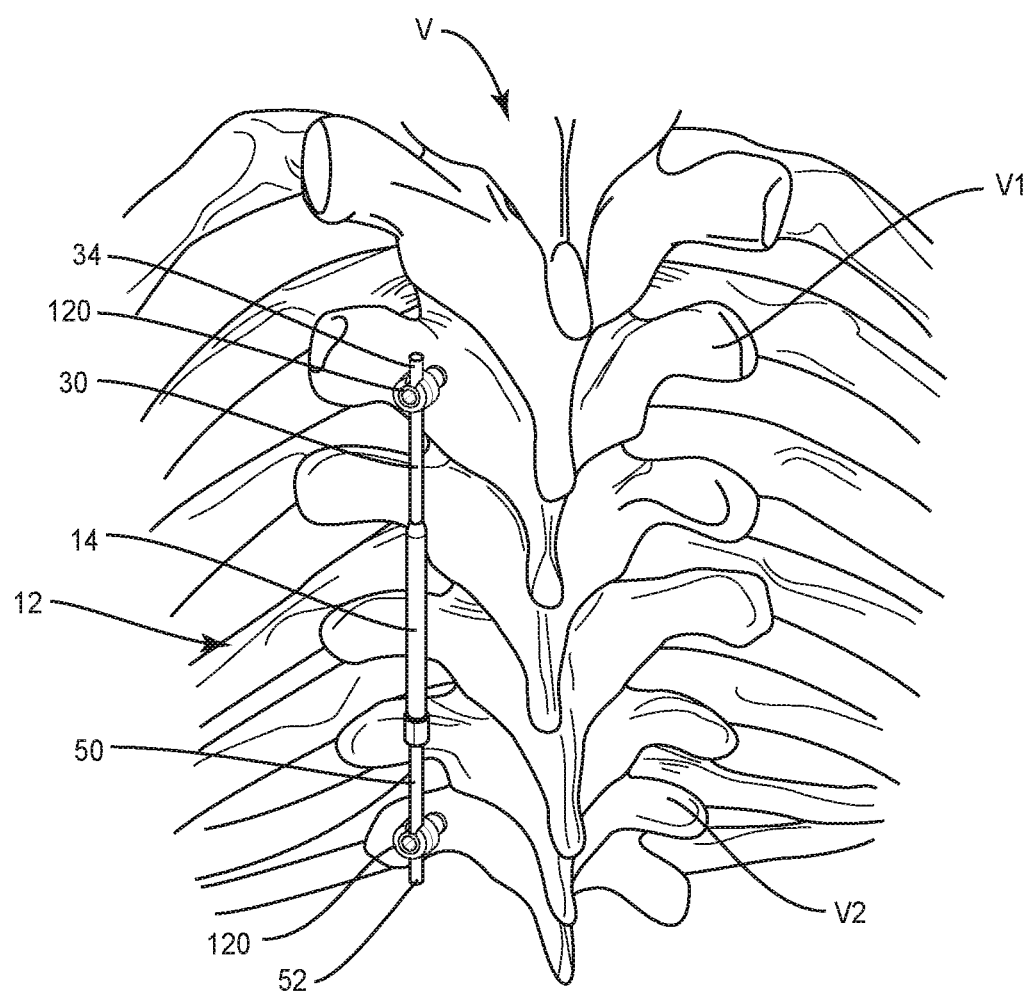
FIG. 4 is a plan view of components of one embodiment of a surgical system in accordance with the principles of the present disclosure disposed with vertebrae.

In some embodiments, spinal construct 12 includes a fastener, such as, for example, a bone fastener 120 that is fastened with vertebrae V, as shown in FIG. 4. In some embodiments, spinal construct 12 may include one or a plurality of fasteners. In some embodiments, one or more of bone fasteners 120 may be engaged with tissue in various orientations, such as, for example, series, parallel, offset, staggered and/or alternate vertebral levels. In some embodiments, one or more fasteners may comprise multi-axial screws, sagittal angulation screws, pedicle screws, monoaxial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Bone fastener 120 comprises a head 122 and an elongated shaft 124 configured for penetrating tissue. Head 122 includes a receiving portion configured for disposal of a longitudinal element, such as, for example, a spinal rod, for example, a rod 30 and/or a rod 50. Rods 30, 50 are attached with and extend along a posterior portion of vertebrae V.

In some embodiments, rod 30 and/or rod 50 are connected with heads 122 causing a tension in rods 30, 50 and/or vertebrae V. In some embodiments, the spinal construct, for example, rods 30, 50 and/or a tension thereof is employed to displace, pull, twist or align vertebrae V as part of a correction system and treatment. In some embodiments, end 52 of rod 50 is fixed with at least one vertebra and end 54 is dynamically moveable within passageway 42. In some embodiments, end 34 of rod 30 is fixed with at least one vertebra.

In some embodiments, spinal construct 12 may include one or more tethers. In some embodiments, rod 30, rod 50 and/or a tether can have a flexible configuration, which includes movement in a lateral or side to side direction and prevents expanding and/or extension in an axial direction upon fixation with vertebrae. In some embodiments, all or only a portion of rod 30, rod 50 and/or a tether may have a semi-rigid, rigid, flexible or elastic configuration, and/or have elastic and/or flexible properties such as the elastic and/or flexible properties corresponding to the material examples described herein. Rod 30, rod 50 and/or a tether can include a plurality of separately attachable or connectable portions or sections, such as bands or loops, or may be monolithically formed as a single continuous element.

In assembly, operation and use, as shown in FIG. 4, spinal correction system 10, similar to the systems and methods described herein, includes spinal construct 12 and is employed with and/or subsequent to a surgical correction procedure, similar to those described herein. Spinal correction system 10 may be employed in surgical procedures for treating disorders of the spine, such as, for example, a correction treatment to treat child/adolescent idiopathic scoliosis and/or Scheuermann's kyphosis of a spine. In some embodiments, one or all of the components of spinal correction system 10 can be delivered as a pre-assembled device or can be assembled in situ.

The surgical correction treatment including spinal construct 12 is used for correction and alignment in stabilization of a treated section of vertebrae V. In use, to create tension along vertebrae V with rods 30, 50, a medical practitioner obtains access to a surgical site including vertebrae V via a posterior surgical approach. In some embodiments, the surgical site may be accessed in any appropriate manner, such as through incision and retraction of tissues. In some embodiments, spinal correction system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area.

In some embodiments, spinal construct 12 includes one or more components, as described herein, disposed in a selected orientation, as described herein, to guide growth along a selected path and/or orientation along vertebrae V, while maintaining a force and/or load on vertebrae V. In some embodiments, one or more components of spinal construct 12 are disposed in a selected orientation, as described herein, to create one or more zones of treatment along vertebrae V. For example, spinal construct 12 can have at least two distracting bodies, as described herein, disposed in sequence to create a treatment zone that increases an extended length, increases force and/or allows for rod contouring. In another example, spinal construct 12 can have at least two distracting bodies, as described herein, having a different spring force such that the differing forces create treatment zones that facilitate distraction of thoracic vertebrae at a different rate than lumbar vertebrae to resist and/or prevent kyphosis of vertebrae V. In another example, spinal construct 12 can have at least two distracting bodies, as described herein, made of different materials to create treatment zones having alternate stiffness and/or flexibility. In some embodiments, the materials of the bodies of spinal construct 12 may have flexible properties, such as the flexible properties corresponding to the material examples described above, and/or may have a semi-rigid, rigid or elastic configuration, and/or have elastic properties, such as the elastic properties corresponding to the material examples described above. In another example, spinal construct 12 can have one or more bodies, as described herein, which create one or more treatment zones to provide opposed distraction. In another example, spinal construct 12 can have at least two distracting bodies, as described herein, fixed to a middle of the spine that create one or more treatment zones to correct an apex curvature, while allowing and guiding growth and maintaining a constant force on vertebrae V. In another example, spinal construct 12 can have one or more bodies, as described herein, fixed to a middle of the spine that create one or more treatment zones to facilitate derotation of vertebrae V. Spinal construct 12 is disposed in a selected orientation with vertebrae V1, V2 in connection with the surgical correction procedure. In some embodiments, one or more spinal constructs 12 are disposed in a linear orientation along vertebrae V. In some embodiments, one or more spinal constructs 12 are disposed with vertebrae V in alternate orientations relative to each other, such as, for example, parallel, perpendicular, adjacent, co-axial, arcuate, offset, staggered, transverse, angular and/or relative posterior/anterior orientations and/or at alternate vertebral levels.

In some embodiments, spinal correction system 10 comprises spinal constructs 12 disposed in a bilateral configuration. For example, a bilateral configuration can include a first spinal construct 12 affixed to a convex side of each of a plurality of vertebrae V and a second spinal construct 12 affixed to a concave side of each of a plurality of vertebrae V. This configuration prevents growth of vertebrae V of the convex side of the spine while allowing for growth and adjustments to the concave side for the correction treatment.

Pilot holes are made in vertebrae V1, V2 of vertebrae V in the selected orientation. Bone fasteners 120, as described herein, are aligned with the pilot holes and fastened with the tissue of vertebrae V1, V2. The components of spinal construct 12 are connected with bone fasteners 120 and disposed in the selected orientation with vertebrae V1, V2.

End 34 of rod 30 is fixed with bone fastener 120 disposed with vertebra V1. Rod 50 is connected with sleeve 14, as described herein, and manipulated to a desired tensioning along vertebrae V. Spinal construct 12 is connected with vertebrae V1, V2 in connection with the correction treatment to facilitate displacing, pulling, twisting and/or aligning vertebrae V as part of spinal correction system 10. End 52 of rod 50 is fixed with bone fastener 120 disposed with vertebra V2 such that spinal construct 12 is disposed in a linear orientation along vertebrae V.

Rod 50 translates, in the direction shown by arrow A in FIG. 2, to expand spinal construct 12 under the bias force of spring 62 to provide a constant pressure to rod 50 for growth guidance and distraction. During growth, biasing member 60 and/or spring 94 react to allow dynamic translation of rod 50 to facilitate growth guidance of spinal construct 12. Rod 50 is dynamically axially translatable relative to sleeve 14 within passageway 42. Dynamic translation of rod 50 allows spinal construct 12 to respond to an active and/or changing spine. As forces and/or force changes are applied to spinal construct 12, for example, patient growth, trauma and degeneration, and/or spinal correction system 10 component creep, deformation, damage and degeneration, rod 50, biasing member 60 and/or spring 94 adapt with a responsive force to maintain the applied force on vertebrae V substantially constant. The biasing force of spring 62 facilitates a self-distracting spinal construct 12. Translation of rod 50 allows spinal construct 12 to selectively adjust its length to accommodate growth to avoid multiple surgeries.

In some embodiments, the components of spinal correction system 10, such as, for example, spinal construct 12, sleeve 14, biasing member 60, spring 94 and/or rods 30, 50, are configured to provide dynamically responsive movement in response to motion of the spine and adjacent anatomical portions due to factors, such as, for example, growth, trauma, aging, natural load bearing and dynamic characteristics of the spine, which may include flexion, extension, rotation and lateral bending, and/or external loads, which may include axial, shear, linear, non-linear, angular, torsional, compressive and/or tensile loads applied to the body of a patient. Lock 70 resists and/or prevents translation of rod 50 relative to sleeve 14, in the direction shown by arrows B in FIG. 2 and/or compression/contraction of the components of spinal construct 12, as described herein.

In some embodiments, the components of spinal correction system 10, such as, for example, spinal construct 12, sleeve 14, biasing member 60, spring 94 and/or rods 30, 50, include force sensors configured to measure the force on the spine and provide feedback to the surgeon. In some embodiments, rods 30, 50 have a low friction/low wear material to eliminate wear debris during expansion and contraction.

In some embodiments, spinal correction system 10 includes an agent, for example, which may be disposed, packed, coated or layered within, on or about the components and/or surfaces of spinal correction system 10. In some embodiments, the agent may include bone growth promoting material, such as, for example, bone graft to enhance fixation of the components and/or surfaces of spinal correction system 10 with vertebrae. In some embodiments, the agent may include one or a plurality of therapeutic agents and/or pharmacological agents for release, including sustained release, to treat, for example, pain, inflammation and degeneration.

Upon completion of a procedure, the surgical instruments and/or tools, assemblies and non-implanted components of spinal correction system 10 are removed and the incision(s) are closed. One or more of the components of spinal correction system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal correction system 10. In some embodiments, spinal correction system 10 may include one or a plurality of rods, plates, connectors and/or bone fasteners for use with a single vertebral level or a plurality of vertebral levels.

In some embodiments, the components of spinal correction system 10 may be employed to treat progressive idiopathic scoliosis with or without sagittal deformity in either infantile or juvenile patients, including but not limited to prepubescent children, adolescents from 10-12 years old with continued growth potential, and/or older children whose growth spurt is late or who otherwise retain growth potential. In some embodiments, the components of spinal correction system 10 and methods of use may be used to prevent or minimize curve progression in individuals of various ages.

Figure 5:
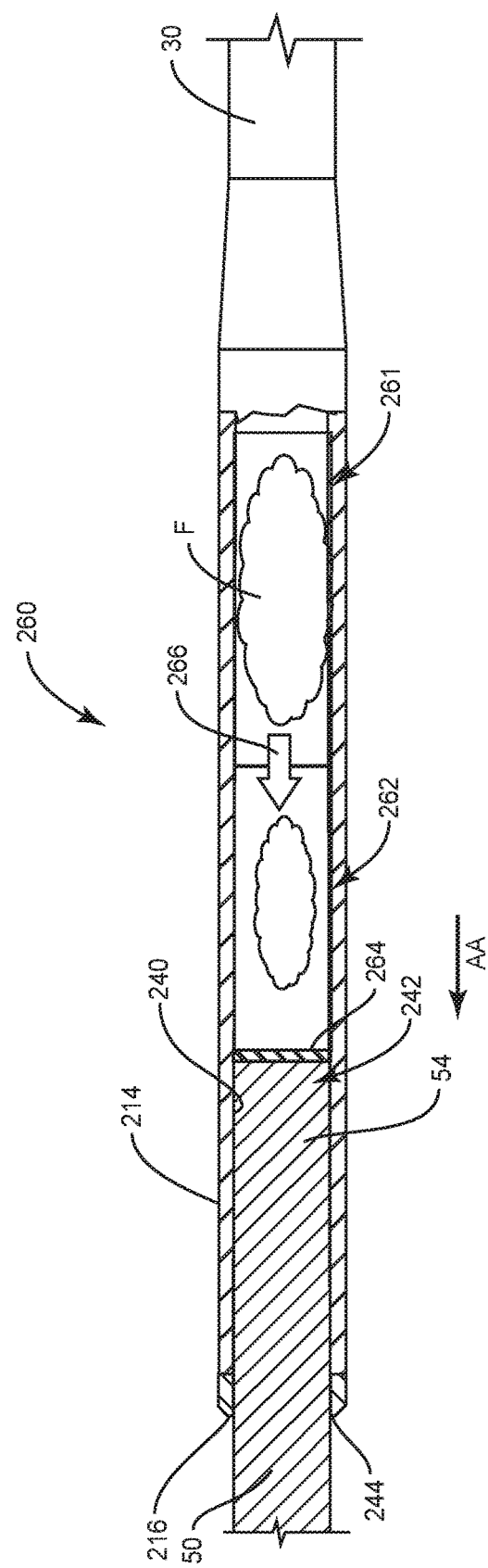
FIG. 5 is a cross section view of components of one embodiment of a surgical system in accordance with the principles of the present disclosure.

In one embodiment, as shown in FIG. 5, spinal correction system 10, similar to the systems and methods described herein, comprises a spinal construct 212, similar to spinal construct 12 described herein. Spinal construct 212 includes a sleeve 214, similar to sleeve 14 described herein, having an inner surface 240 that defines a passageway 242. Passageway 242 includes an opening 244 adjacent an end 216. Passageway 242 and opening 244 are configured for movable disposal of spinal rod 50 described herein. Rod 50 is dynamically translatable within passageway 242 relative to sleeve 214, similar to that described herein.

Rod 50 is configured for connection with a biasing member 260, similar to biasing member 60 described herein. Biasing member 260 includes a high pressure chamber 261 and a low pressure chamber 262. Biasing member 260 includes a wall 264 that is connected with low pressure chamber 262 and end 54 of rod 50. In some embodiments, wall 264 comprises a piston disposed with low pressure chamber 262.

Biasing member 260 includes a fluid F, such as, for example, a pressurized biomaterial and/or a pressurized expanding medium that is disposed with high pressure chamber 261 and configured to flow and/or expand from chamber 261 to low pressure chamber 262 via a one-way valve 266. Valve 266 is configured to allow transfer of fluid F from high pressure chamber 261 to low pressure chamber 262, and to resist and/or prevent transfer of fluid F from low pressure chamber 262 to high pressure chamber 261. In some embodiments, valve 266 resists and/or prevents transfer of fluid F from low pressure chamber 262 to high pressure chamber 261 such that spinal construct 212 is self-locking. Pressurized fluid F maintains a constant pressure and/or force applied to wall 264, as described herein, including during relative translation of rod 50, which may modify or increase a volume of chamber 262. In some embodiments, fluid F may include silicone, injectable polymer, sterile water, saline, inflating air and/or other fluids and gases, and/or combinations thereof. In some embodiments, fluid F is introduced from high pressure chamber 261 to low pressure chamber 262 via valve 266 at a pressure in a range of 3 pounds per square inch (psi) to 5000 psi. In some embodiments, fluid F may be introduced from high pressure chamber 261 to low pressure chamber 262 via valve 266 at constant or varied pressure. In some embodiments, valve 266 is movable between a vent position and a seal position to facilitate transfer of fluid F.

Wall 264 is configured for moveable disposal within sleeve 214 and driven or urged in a selected direction under the bias force of pressurized fluid F disposed with low pressure chamber 262 to facilitate translation of rod 50, as described herein. Pressurized fluid F disposed with low pressure chamber 262 applies a force to wall 264 causing wall 264 to drive and/or urge rod 50 in a direction, as shown by arrow AA in FIG. 5. In some embodiments, pressurized fluid F facilitates dynamic translation of rod 50 during growth, as described herein. Dynamic translation of rod 50 allows spinal construct 212 to respond to an active and/or changing spine. For example, as forces and/or force changes are applied to spinal construct 212, such as, for example, patient growth, trauma and degeneration, and/or spinal correction system 10 component creep, deformation, damage and degeneration, one or more components of spinal construct 212, for example, sleeve 214, rod 50 and biasing member 260 adapt with a responsive force to maintain the applied force transmitted from the bone fasteners substantially constant. In some embodiments, spinal construct 212 includes biasing member 260 and lock 70 disposed with surface 240, similar to that described herein.

Figure 6:
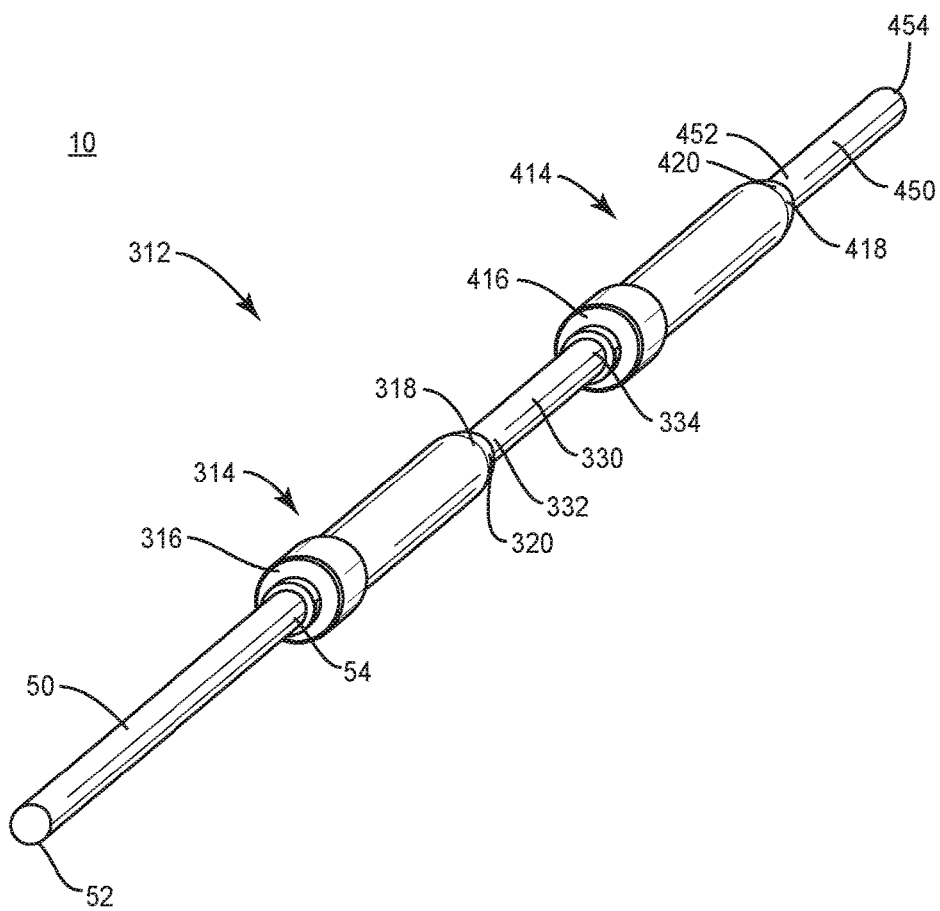
FIG. 6 is a perspective view of components of one embodiment of a surgical system in accordance with the principles of the present disclosure.
Figure 7:
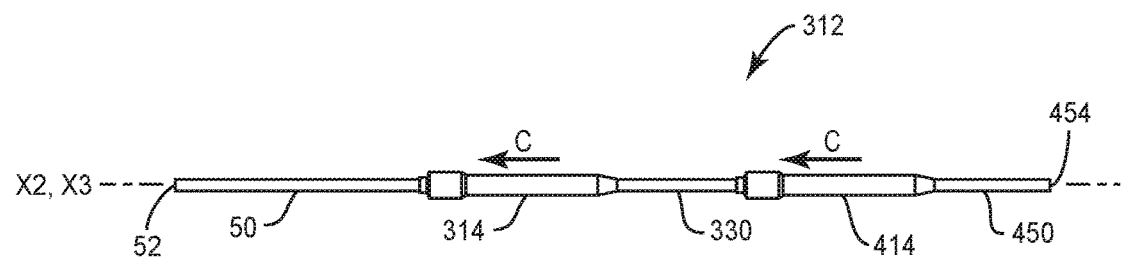
FIG. 7 is a plan view of the components shown in FIG. 6.

In one embodiment, as shown in FIGS. 6 and 7, spinal correction system 10, similar to the systems and methods described herein, comprises a spinal construct 312, similar to spinal construct 12 described herein. Spinal construct 312 includes one or more components, as described herein, disposed in a selected orientation, as described herein, to guide growth along a selected path and/or orientation along vertebrae, while maintaining a load on vertebrae. In some embodiments, one or more components of spinal construct 312 are disposed in a selected orientation with vertebrae in connection with a surgical correction procedure to create one or more zones of treatment along vertebrae, similar to that described herein.

Spinal construct 312 includes a body having a sleeve 314, similar to sleeve 14 described herein. Sleeve 314 defines a longitudinal axis X2. Sleeve 314 extends between an end 316 and an end 318. The body of spinal construct 312 includes a rod 330, similar to rod 30 described herein, extending from end 318. Rod 330 extends between an end 332 and an end 334. An outer surface 320 of sleeve 314 tapers between end 318 and rod 330 such that rod 330 includes a smaller dimension, such as, for example, a diameter in thickness than sleeve 314. End 334 is configured for disposal with a passageway of a sleeve 414, similar to sleeve 14 described herein.

Sleeve 314 includes an inner surface (not shown) that defines a passageway (not shown), similar to passageway 42, as described herein. The passageway of sleeve 314 is configured for movable disposal of rod 50, as described herein. Rod 50 is configured to translate within the passageway relative to sleeve 314, similar to that described herein. Rod 50 is engageable with a lock (not shown), similar to lock 70 described herein, to resist and/or prevent translation of rod 50 relative to sleeve 314. End 54 is configured for disposal within the passageway of sleeve 314. End 54 is configured for connection with a biasing member (not shown), similar to biasing member 60 described herein.

Spinal construct 312 includes sleeve 414, which defines a longitudinal axis X3. Sleeve 414 extends between an end 416 and an end 418. Sleeve 414 includes an inner surface (not shown) that defines a passageway (not shown), similar to passageway 42 described herein. The passageway of sleeve 414 is configured for movable disposal of rod 330, similar to that described herein. Rod 330 is engageable with a lock (not shown), similar to lock 70 described herein, disposed with sleeve 414 to resist and/or prevent translation of rod 330 relative to sleeve 414.

Sleeve 414 includes a rod 450, similar to rod 30 described herein, extending from end 418. Rod 450 extends between an end 452 and an end 454. An outer surface 420 of sleeve 414 tapers between end 418 and rod 450 such that rod 450 includes a smaller diameter than sleeve 414. End 454 is configured for engagement with tissue and/or a spinal implant, such as, for example, a bone fastener, similar to that described herein.

Spinal construct 312 is disposed in a selected orientation, for example, sleeves 314, 414 are oriented in sequence and/or a serial configuration to guide growth along a selected path and/or orientation along vertebrae, while maintaining a load on vertebrae in connection with a surgical correction procedure, similar to that described herein. Sleeve 314 is oriented in series with sleeve 414 such that axis X2 is in alignment with axis X3, as shown in FIG. 7. In some embodiments, sleeves 314, 414 are disposed in a serial orientation to create a treatment zone that extends a length of spinal construct 312, increases force or force resistance to vertebrae and/or allows for rod contouring of the components of spinal construct 312.

Rods 50, 330 are configured for dynamic translation during growth, similar to that described herein. Dynamic translation of rods 50, 330, in the same direction, as shown by arrows C in FIG. 7, allows spinal construct 312 to provide concurrent extension and/or expansion of its components and respond to an active and/or changing spine, similar to that described herein. In some embodiments, the biasing members disposed with sleeves 314, 414 are configured with different spring forces and/or rates to create treatment zones. In some embodiments, the treatment zones can comprise a zone that facilitates distraction of a first region of spinal construct 12 disposed adjacent, for example, a thoracic portion of the spine at a first rate and a zone that facilitates distraction of a second region of spinal construct 12 disposed adjacent, for example, a lumbar portion of the spine at a second, different rate. In some embodiments, the zones provide a varied rate of distraction in the same direction, as shown by arrows C in FIG. 7. In some embodiments, this configuration resists and/or prevents kyphosis. In some embodiments, rod 50 may include a different material from rod 330 and/or rod 450 to create treatment zones that alter a stiffness of spinal construct 312, for example, spinal construct 312 may be more flexible adjacent rod 50.

Figure 8:
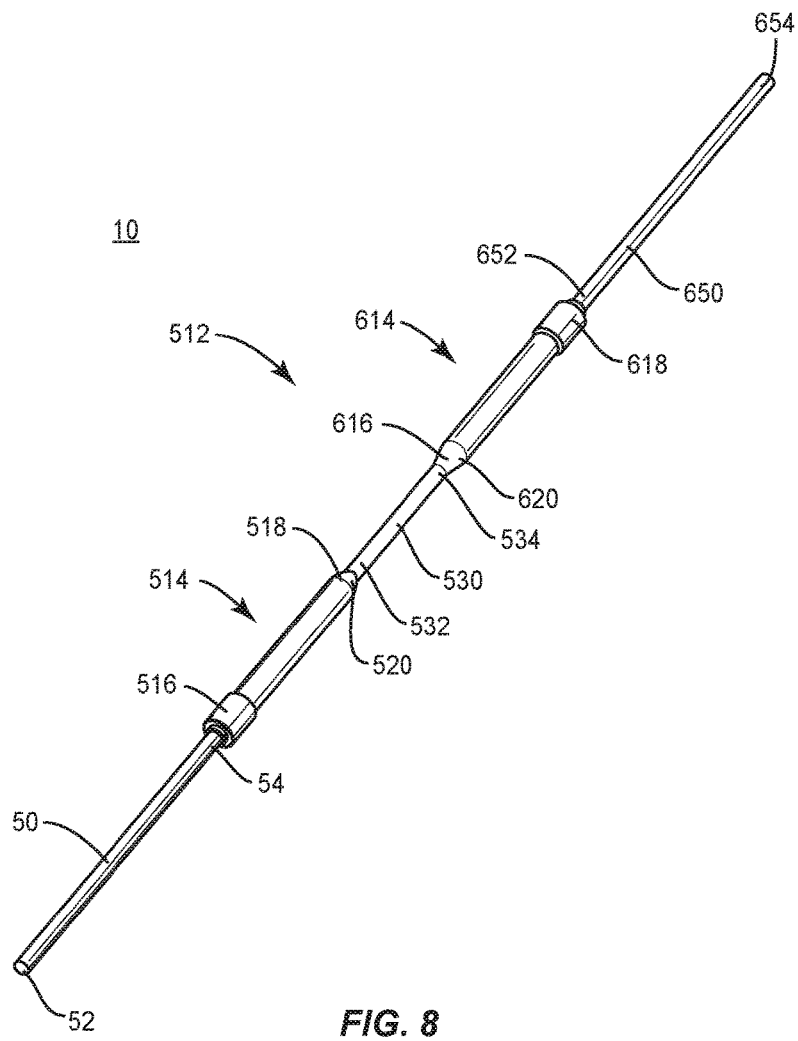
FIG. 8 is a perspective view of components of one embodiment of a surgical system in accordance with the principles of the present disclosure.
Figure 9:
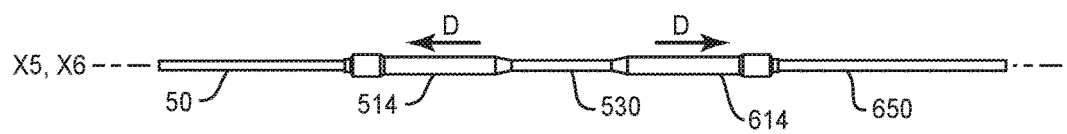
FIG. 9 is a plan view of the components shown in FIG. 8.
Figure 10:
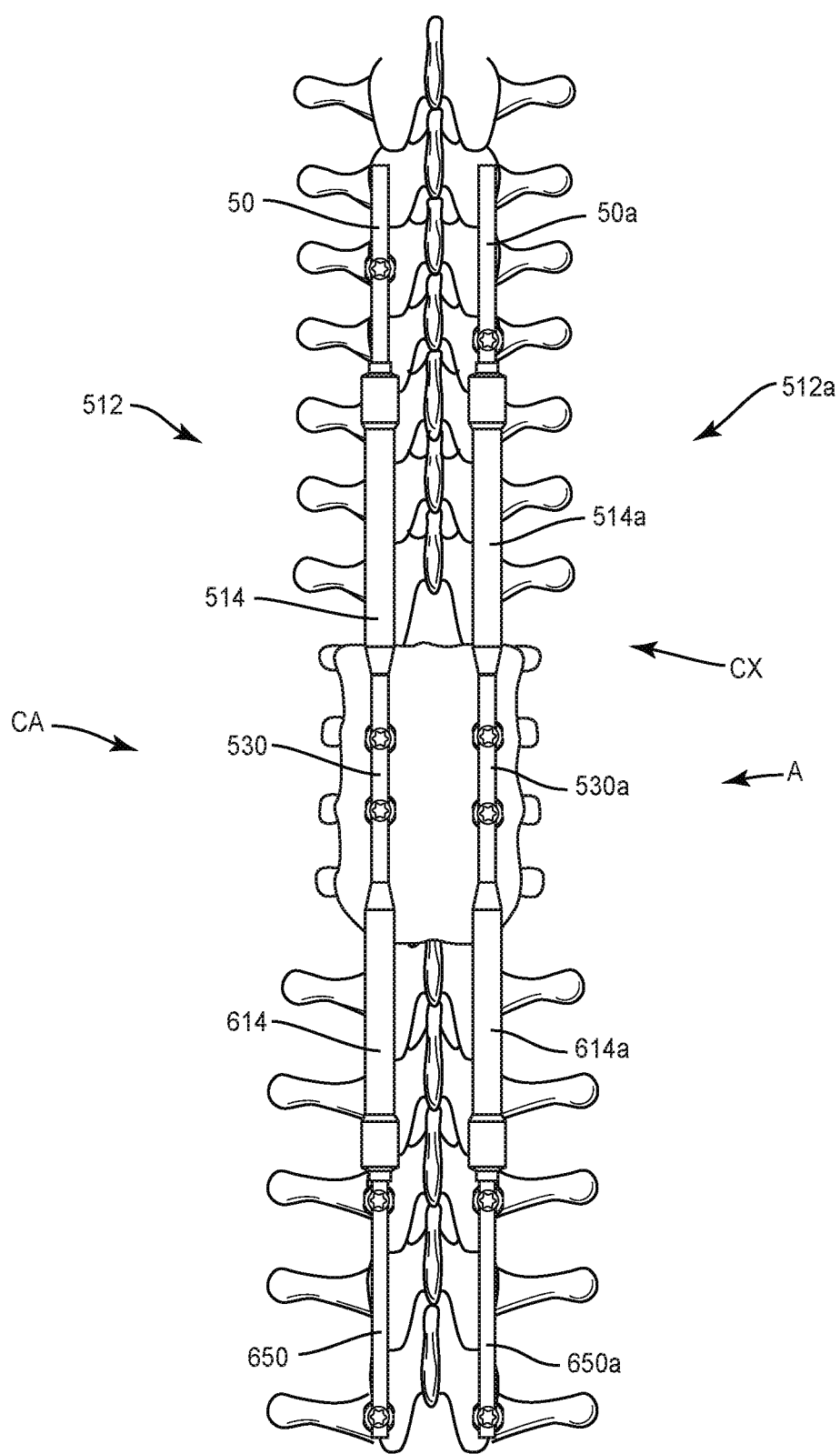
FIG. 10 is a plan view of components of one embodiment of a surgical system in accordance with the principles of the present disclosure disposed with vertebrae.

In one embodiment, as shown in FIGS. 8-10, spinal correction system 10, similar to the systems and methods described herein, comprises a spinal construct 512, similar to spinal construct 12 described herein. Spinal construct 512 includes one or more components, as described herein, disposed in a selected orientation, as described herein, to guide growth along a selected path and/or orientation along vertebrae, while maintaining a load on vertebrae. In some embodiments, one or more components of spinal construct 512 are disposed in a selected orientation with vertebrae in connection with a surgical correction procedure to create one or more zones of treatment along vertebrae, similar to that described herein.

Spinal construct 512 includes a body having a sleeve 514, similar to sleeve 14 described herein. Sleeve 514 defines a longitudinal axis X5. Sleeve 514 extends between an end 516 and an end 518. The body of spinal construct 512 includes a rod 530, similar to rod 30 described herein, extending from end 518. Rod 530 extends between an end 532 and an end 534. End 532 is monolithically formed with sleeve 514. End 534 is configured for connection with a sleeve 614, similar to sleeve 14 described herein.

Sleeve 514 includes an inner surface (not shown) that defines a passageway (not shown), similar to passageway 42 described herein. The passageway of sleeve 514 is configured for movable disposal of rod 50 described herein. Rod 50 is configured to translate within the passageway relative to sleeve 514, similar to that described herein. Rod 50 is engageable with a lock (not shown), similar to lock 70 described herein, to resist and/or prevent translation of rod 50 relative to sleeve 514. End 54 is configured for disposal within the passageway of sleeve 514. End 54 is configured for connection with a biasing member (not shown), similar to biasing member 60 described herein.

Spinal construct 512 includes sleeve 614, which defines a longitudinal axis X6. Sleeve 614 extends between an end 616 and an end 618. End 534 of rod 530 extends from end 616. End 534 is monolithically formed with sleeve 614. In some embodiments, rod 530 is integrally connected or includes fastening elements for connection with sleeve 614. An outer surface 620 of sleeve 614 tapers between end 618 and rod 530 such that rod 530 includes a smaller diameter than sleeve 614.

Sleeve 614 includes an inner surface that defines a passageway (not shown), similar to passageway 42 described herein. The passageway of sleeve 614 is configured for movable disposal of a rod 650, similar to rod 50 described herein. Rod 650 extends between an end 652 and an end 654. End 652 is engageable with a lock (not shown), similar to lock 70 described herein, to resist and/or prevent translation of rod 650 relative to sleeve 614. End 654 is configured for engagement with tissue and/or a spinal implant, such as, for example, a bone fastener, as described herein.

End 652 is configured for disposal within the passageway of sleeve 614. End 652 is configured for connection with a biasing member (not shown), similar to biasing member 60 described herein. Rod 650 is configured to translate within the passageway relative to sleeve 614.

Spinal construct 512 is disposed in a selected orientation, for example, sleeves 514, 614 are oriented in opposing relation to guide growth along a selected path and/or provide opposed distraction along vertebrae, while maintaining a load on vertebrae in connection with a surgical correction procedure, similar to that described herein. Sleeve 514 is oriented in opposing relation with sleeve 614 such that axis X5 is in alignment with axis X6, as shown in FIG. 9. Rods 50, 650 are configured for dynamic translation during growth, similar to that described herein. Dynamic translation of rods 50, 650, in opposing directions, as shown by arrows D in FIG. 9, allows spinal construct 512 to create a treatment zone that provides opposed distraction and/or expansion of its components and responds to an active and/or changing spine, similar to that described herein.

In one example, bone fasteners 120 are engaged with vertebrae including fixation adjacent an apex A of a spinal curvature, as shown in FIG. 10. Spinal correction system 10 is disposed in a bilateral configuration including, such as, for example, a spinal construct 512 and a spinal construct 512*a*. Spinal construct 512*a* is affixed to a convex side CX of each of a plurality of vertebrae. Spinal construct 512 is affixed to a concave side CA of each of a plurality of vertebrae. This configuration prevents growth of vertebrae of convex side CX of the spine while allowing for growth and adjustments to concave side CA for a correction treatment to treat various spine pathologies, such as, for example, adolescent idiopathic scoliosis and Scheuermann's kyphosis.

Spinal constructs 512, 512*a* are disposed in a selected orientation such that each of spinal constructs 512, 512*a* includes sleeves 514, 614 oriented in opposing relation to guide growth along a selected path and/or provide opposed distraction along vertebrae, while maintaining a load on vertebrae in connection with a surgical correction procedure, as described herein. The opposing forces of the biasing members of sleeves 514, 614, as described herein, create treatment zones that facilitate correction of vertebrae adjacent apex A, while guiding growth. Dynamic translation of rods 50, 650, as described herein, allows spinal constructs 512, 512*a* to respond to an active and/or changing spine. In some embodiments, rods 50, 650 may be keyed to sleeves 514, 614 to facilitate derotation of vertebrae. In some embodiments, spinal constructs 512, 512*a* include a pre-selected curvature having a selected kyphotic curve, which may include curvature in a sagittal plane.

Figure 11:
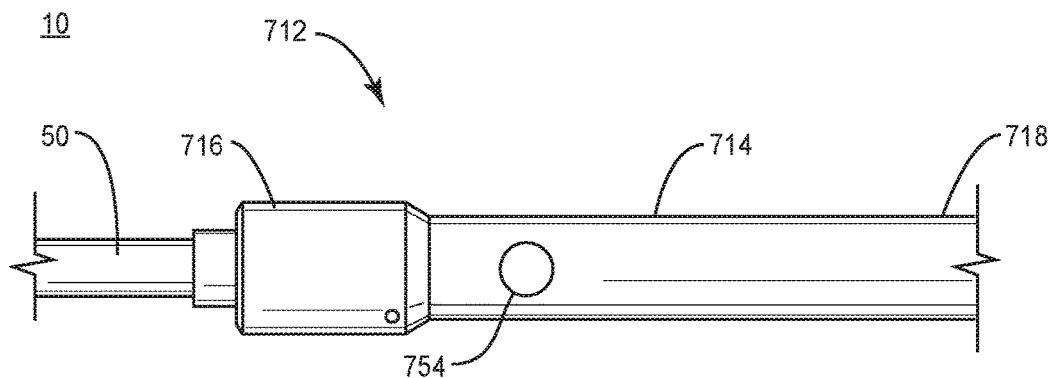
FIG. 11 is a break away view of components of one embodiment of a surgical system in accordance with the principles of the present disclosure.
Figure 12:
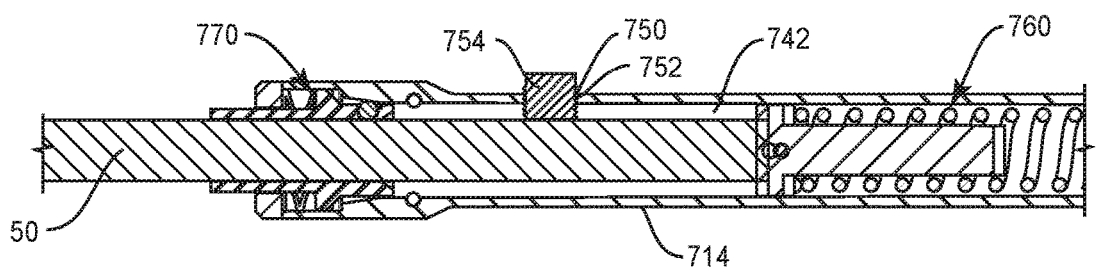
FIG. 12 is a cross section view of the components shown in FIG. 11.

In one embodiment, as shown in FIGS. 11 and 12, spinal correction system 10, similar to the systems and methods described herein, comprises a spinal construct 712, similar to spinal construct 12 described herein. Spinal construct 712 includes a body having a sleeve 714, similar to sleeve 14 described herein. Sleeve 714 extends between an end 716 and an end 718. The body of spinal construct 712 includes a rod (not shown), similar to rod 30 described herein. Sleeve 714 defines a passageway 742, similar to passageway 42 described herein. Passageway 742 is configured for movable disposal of rod 50 described herein. Rod 50 is configured to translate within passageway 742 relative to sleeve 714 via a biasing member 760, similar to biasing member 60 described herein, and is engageable with a lock 770, similar to lock 70 described herein.

Sleeve 714 includes a surface 750 that defines an opening 752. Opening 752 is configured for engagement with a release member, such as, for example, a set screw 754. Set screw 754 is engageable with sleeve 714 and rod 50 to dispose spinal construct 712 in a selected configuration, setting and/or position. Set screw 754 is engageable with a surface of rod 50 to facilitate delivery of spinal construct 712 to a surgical site such as an operating room, back table, medical facility and/or with a patient body. Set screw 754 is threadably engageable with sleeve 714 to connect, attach, fix and/or lock, provisionally, removably and/or permanently, rod 50 to sleeve 714 in a selected configuration, setting and/or position of spinal construct 712.

For example, spinal construct 712 can be disposed in a selected configuration, setting and/or position for delivery of spinal construct 712 to a surgical site. Rod 50 is contracted, collapsed and/or compressed with biasing member 760 within sleeve 714 to dispose spinal construct 712 in a contracted, collapsed and/or compressed configuration. Set screw 754 is engaged with sleeve 714 and rod 50 to provisionally fix rod 50 in a non-expandable, contracted, collapsed and/or compressed configuration relative to sleeve 714 for delivery of spinal construct 712 to a surgical site. In some embodiments, set screw 754 may engage the components of spinal construct 712 in a friction fit, pressure fit, interference, mating engagement, interlock and/or adhesive. Spinal construct 712 is attached with vertebrae, similar to spinal construct 12 described herein. Set screw 754 is rotated, disengaged and/or removed from the components of spinal construct 712 intra-operatively in a controlled manner to avoid unexpected forces being applied to the vertebrae. In some embodiments, set screw 754 may disengage or be removed from the components of spinal construct 712 gradually. Disengagement or removal of set screw 754 from the components of spinal construct 712 releases spinal construct 712 from the selected configuration, setting and/or position to activate and/or release rod 50 such that rod 50 can dynamically translate and/or expand spinal construct 712, similar to that described herein. In some embodiments, spinal correction system 10 includes a release mechanism engageable with the components of spinal construct 712 and is resorbable at precise time periods to initiate a next phase of growth of vertebrae.

Figure 13:
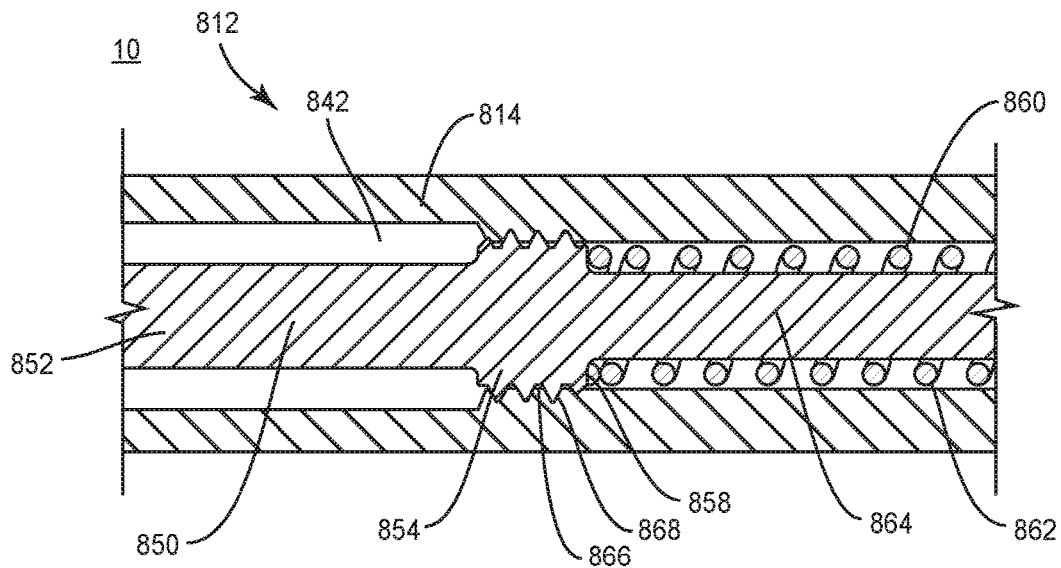
FIG. 13 is a cross section view of components of one embodiment of a surgical system in accordance with the principles of the present disclosure.

In one embodiment, as shown in FIG. 13, spinal correction system 10, similar to the systems and methods described herein, comprises a spinal construct 812, similar to spinal construct 12 described herein. Spinal construct 812 includes a body having a sleeve 814, similar to sleeve 14 described herein. Sleeve 814 extends between an end 816 and an end 818. The body of spinal construct 812 includes a rod (not shown), similar to rod 30 described herein. Sleeve 814 defines a passageway 842, similar to passageway 42 described herein. Passageway 842 is configured for movable disposal of a rod 850, similar to rod 50 described herein. Rod 850 is configured to translate within passageway 842 relative to sleeve 814, similar to that described herein.

Rod 850 extends between an end 852 and an end 854. End 854 is configured for disposal within passageway 842. End 854 includes a surface 858 configured for connection with a biasing member 860, similar to biasing member 60 described herein. Biasing member 860 includes a coil spring 862 and a follower 864. Follower 864 is configured for moveable disposal within sleeve 814 and driven or urged in a selected direction under the bias force of spring 862 to facilitate translation of rod 850.

Follower 864 includes a surface 866 that is threaded with a surface 868 of sleeve 814 to comprise a release member of spinal construct 812. Surface 866 is threaded with sleeve 814 in a selected configuration, setting and/or position to facilitate delivery of spinal construct 812 to a surgical site such as an operating room, back table, medical facility and/or with a patient body. Surface 866 is threaded with sleeve 814 to connect, attach, fix and/or lock, provisionally, removably and/or permanently, rod 50 to sleeve 814 in a selected configuration, setting and/or position of spinal construct 812.

For example, spinal construct 812 can be disposed in a selected configuration, setting and/or position for delivery of spinal construct 812 to a surgical site. Rod 50 is contracted, collapsed and/or compressed with biasing member 860 within sleeve 814 to dispose spinal construct 812 in a contracted, collapsed and/or compressed configuration. Surface 866 is engaged with sleeve 814 in a configuration with rod 50 to provisionally fix rod 50 in a non-expandable, contracted, collapsed and/or compressed configuration relative to sleeve 814 for delivery of spinal construct 812 to a surgical site. Spinal construct 812 is attached with vertebrae, similar to spinal construct 12 described herein. Surface 866 is rotated to disengage surfaces 866, 868 intra-operatively in a controlled manner to avoid unexpected forces being applied to the vertebrae and allow relative movement of rod 50 and sleeve 814. Disengagement of surfaces 866, 868 releases spinal construct 812 from the selected configuration, setting and/or position to activate and/or release rod 50 such that rod 50 can dynamically translate and/or expand spinal construct 812, similar to that described.

Figure 16:
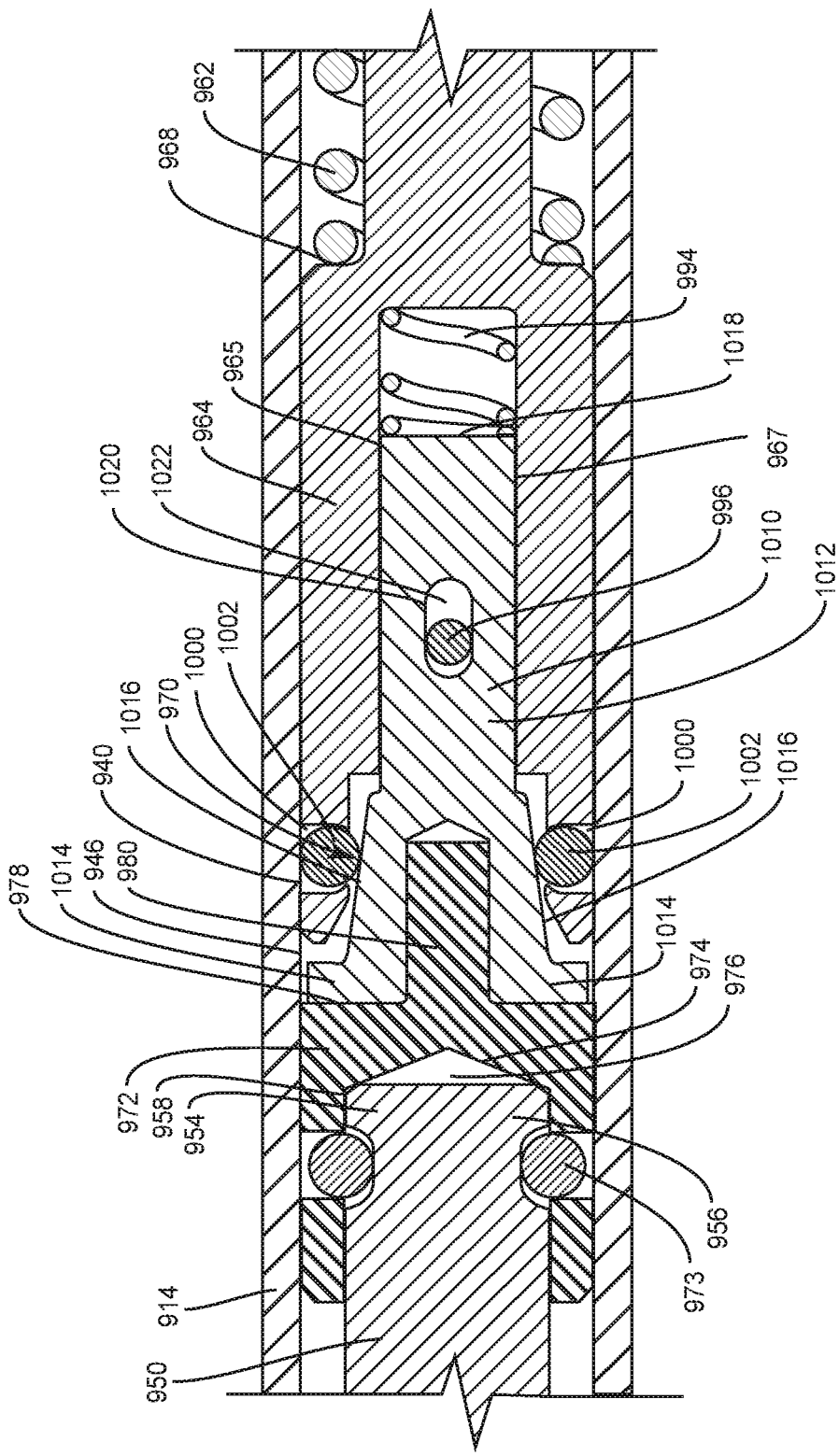
FIG. 16 is an exploded view of the components shown in FIG. 15.

In one embodiment, as shown in FIGS. 14-16, spinal correction system 10, similar to the systems and methods described herein, comprises a spinal construct 912, similar to spinal construct 12 described herein. Spinal construct 912 includes a body having a sleeve 914, similar to sleeve 14 described herein.

Sleeve 914 defines a longitudinal axis X9. Sleeve 914 extends between an end 916 and an end 918. The body of spinal construct 912 includes a rod 930 extending from end 918. Rod 930 extends between an end 932 and an end 934. In some embodiments, end 932 is monolithically formed with sleeve 914. End 934 is configured for engagement with tissue and/or a spinal implant, such as, for example, a bone fastener, as described herein.

Sleeve 914 includes a surface 940 that defines a passageway 942, similar to passageway 42 described herein. Passageway 942 extends axially within sleeve 914. Passageway 942 includes an opening 944 adjacent end 916. Passageway 942 and opening 944 are configured for movable disposal of a spinal rod 950, similar to rod 50 described herein. Rod 950 is configured to translate within passageway 942 relative to sleeve 914, as described herein. In some embodiments, rod 950 is configured for dynamic axial translation relative to sleeve 914, as described herein. Surface 940 defines a cavity 946 for disposal of a portion of a lock 970, similar to lock 70 described herein.

Rod 950 extends between an end 952 and an end 954. Rod 950 includes a surface 956 engageable with an inner surface of lock 970 to facilitate translation of rod 950 relative to sleeve 914 in a first direction and to resist and/or prevent translation of rod 950 in a second direction, as described herein. End 952 is configured for engagement with tissue and/or a spinal implant, such as, for example, a bone fastener, as described herein. End 954 is configured for disposal within passageway 942. End 954 includes a surface 958 configured for connection with a portion of lock 970, as shown in FIG. 16.

A biasing member 960, similar to biasing member 60 described herein, includes a spring 962 and a follower 964. Follower 964 is configured for moveable disposal within sleeve 914 and driven or urged in a selected direction under the bias force of spring 962 to facilitate translation of rod 950, as described herein. In some embodiments, such translation of rod 950 includes expansion of spinal construct 912 under the bias force of spring 962 to provide a constant pressure to rod 950 for growth guidance and distraction.

In some embodiments, follower 964 includes a surface 965. Surface 965 defines a cavity 967 configured for disposal of a portion of lock 970, as described herein. In some embodiments, follower 964 includes openings 1000 configured for disposal of bearings 1002. Bearings 1002 are configured to roll and/or slide between surface 940 and a tapered portion 1016 of lock 970 to facilitate translation of rod 950 relative to sleeve 914, and/or expansion of the components of spinal construct 912, as described herein.

Spring 962 is disposed within sleeve 914 and extends between a surface 963 of sleeve 914 and a surface 968 of follower 964. In some embodiments, spring 962 extends about an extension 969 of follower 964. Spring 962 applies a force and/or load to surface 968 causing follower 964 to drive and/or urge rod 950, as described herein. As such, rod 950 is urged to expand spinal construct 912 under a constant force of spring 962. In some embodiments, spring 962 facilitates dynamic translation of rod 950 during growth. Dynamic translation of rod 950 allows spinal construct 912 to respond to an active and/or changing spine.

For example, as forces and/or force changes are applied to spinal construct 912, such as, for example, patient growth, trauma and degeneration, and/or system 10 component creep, deformation, damage and degeneration, one or more components of spinal construct 912, for example, sleeve 914, rod 950 and biasing member 960 adapt and/or are continuously adjustable with a responsive force to maintain the applied force transmitted from the bone fasteners substantially constant.

In some embodiments, the dynamic biasing force of spring 962 facilitates a self-distracting spinal construct 912. Translation of rod 950 allows spinal construct 912 to selectively adjust its length to accommodate growth to avoid multiple surgeries. In some embodiments, spinal construct 912 includes one or more components, as described herein, disposed in a selected orientation, as described herein, to guide growth along a selected path, while maintaining a load on the spine.

Lock 970 includes a sleeve 972 having an inner surface 974 that defines a cavity 976. Rod 950 is configured for disposal within cavity 976. In some embodiments, rod 950 is connected with sleeve 972 and includes bearings 973 to facilitate relative rotation of rod 950, as shown in FIG. 16. Sleeve 972 includes a surface 978 that includes an extension 980. Extension 980 is configured for disposal with a locking member 1010. Member 1010 includes an extension 1012 and a receiver 1014. Extension 1012 is configured for disposal with cavity 967. Receiver 1014 includes tapered portion 1016 configured for engagement with bearings 1002, as described herein. In some embodiments, tapered portion 1016 may include a constant taper throughout a length. In some embodiments, tapered portion 1016 extends along a discrete length of receiver 1014. In some embodiments, tapered portion 1016 includes a substantially continuous slope, or may include different slopes along the length.

Lock 970 includes a biasing member, such as, for example, a coil spring 994, as shown in FIG. 16. Spring 994 is disposed within cavity 967. Spring 994 applies a force and/or load to a surface 1018 of member 1010. In some embodiments, spring 994 stabilizes motion and/or positions lock 970 with passageway 942. In some embodiments, spring 994 causes lock 970 to drive and/or urge rod 950, as described herein. As such, in the non-locked orientation rod 950 is urged to expand spinal construct 912 under a constant force of springs 962, 994. In some embodiments, springs 962, 994 facilitate dynamic translation of rod 950 during growth. Dynamic translation of rod 950 allows spinal construct 912 to respond to an active and/or changing spine.

Upon compression and/or contraction of the components of spinal construct 912, bearings 1002 slide/roll into a more narrow space between surfaces 1016 and 940 for an interference and/or frictional engagement therewith to compress and/or crimp rod 950 with tapered portion 1016 to resist and/or prevent translation of rod 950 relative to sleeve 914 and/or compression/contraction of the components of spinal construct 912, as described herein. In some embodiments, translation of rod 950 relative to sleeve 914 and/or compression/contraction of the components of spinal construct 912 is resisted and/or prevented in a locked orientation of spinal construct 912. In some embodiments, lock 970 is disengageable or removable from a locked orientation. In some embodiments, lock 970 is fixed in a locked orientation.

In some embodiments, spinal construct 912 prevents axial migration of rod 950 while maintaining a dynamically movable configuration of rod 950. In some embodiments, rod 950 may include a dynamically axially translatable configuration, as described herein, and spinal construct 912 may be configured, as described herein, such that spinal construct 912 may limit, resist and/or prevent movement in at least one direction of rod 950 relative to sleeve 914. Movement of bearings 1002 along tapered portions 1016 facilitates locking and unlocking of lock 970 relative to rod 950.

In some embodiments, member 1010 includes a surface 1020 that defines a slot 1022. In some embodiments, slot 1022 is configured for engagement with a pin 996 to connect sleeve 914 with lock 970. In some embodiments, pin 996 and slot 1022 are configured to guide movement of rod 950 and/or lock 970. In some embodiments, pin 996 and slot 1022 define a range of movement of translation of member 1010.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   a longitudinal element
   at least one body including a follower and a first biasing member disposed about the body, the longitudinal element being movably disposed in the body, the follower being connected to the longitudinal element by a pin that extends through the follower and the longitudinal element, the first biasing member applying a force to the follower such that the follower translates the longitudinal element relative to the body in a first direction; and
   a second biasing member engageable with a lock disposed with the at least one body, the second biasing member including a sheath and a flange fixed to the sheath, the second biasing member comprising a first end directly engaging the flange and an opposite second end directly engaging an end wall of the body, the lock being connected with the longitudinal element to resist and/or prevent translation of the longitudinal element relative to the body in a second direction.

2. A spinal construct as recited in claim 1, wherein the first biasing member and the lock comprise a strut to resist and/or prevent translation of the longitudinal element in the second direction.

3. A spinal construct as recited in claim 1, wherein the longitudinal element includes a first end configured to be connected with vertebral tissue and a second end connected with the follower such that the second end is continuously adjustable relative to the body.

4. A spinal construct as recited in claim 1, wherein the longitudinal element includes a first end configured to be connected with vertebral tissue and a second end connected with the follower such that the second end is dynamically translatable relative to the body.

5. A spinal construct as recited in claim 1, wherein the body includes an inner surface having a tapered portion engageable with the lock in a crimp configuration.

6. A spinal construct as recited in claim 1, wherein the lock includes a plurality of spaced apart bearings engageable with the body to resist and/or prevent translation of the longitudinal element relative to the body in the second direction.

7. A spinal construct as recited in claim 1, further comprising a release mechanism engageable with the at least one body and the longitudinal element to fix the longitudinal element in a non-expandable and/or compressed orientation relative to the at least one body.

8. A spinal construct as recited in claim 7, wherein the release mechanism is disengageable from the at least one body and the longitudinal element intra-operatively.

9. A spinal construct as recited in claim 1, wherein the flange is configured to engage the end wall to prevent translation of the longitudinal element relative to the body in the first direction.

10. A spinal construct as recited in claim 1, wherein the body includes a stop facing the end wall, the flange being configured to engage the stop to prevent translation of the longitudinal element relative to the body in the second direction.

11. A spinal construct as recited in claim 1, wherein the sheath defines a longitudinal axis, the flange having a first surface that extends at an acute angle relative to the longitudinal axis and a second surface that extends perpendicular to the longitudinal axis.

12. A spinal construct as recited in claim 11, wherein the body includes a stop facing the end wall, the first surface being configured to engage the stop to prevent translation of the longitudinal element relative to the body in the second direction, the second surface being configured to engage the end wall to prevent translation of the longitudinal element relative to the body in the first direction.

13. A spinal construct as recited in claim 1, wherein the body includes an inner surface having a tapered portion, the sheath comprising a plurality of openings and a bearing disposed each of the openings, the bearings being configured to slide between an outer surface of the longitudinal element and the tapered portion to crimp the longitudinal element with the tapered portion to resist and/or prevent translation of the longitudinal element relative to the body in the second direction.

14. A spinal construct as recited in claim 1, wherein the body includes a groove and a ring disposed in the groove, the lock including a range of movement and the ring defining a limit to facilitate limitation of translation of the longitudinal element in the second direction.

15. A spinal construct comprising:
    a rod;
    a sleeve including a follower and a spring disposed thereabout, the rod being disposed in the sleeve, the follower being connected to the rod by a pin that extends through the follower and the rod, the spring applying a force to the follower such that the follower translates the rod relative to the sleeve in a first axial direction; and
    a lock spring engageable with a lock disposed with the sleeve, the lock comprising a sheath and a flange fixed to the sheath, the lock spring comprising a first end directly engaging the flange and an opposite second end directly engaging an end wall of the sleeve, the lock being connected with the rod to resist and/or prevent translation of the rod relative to the sleeve in a second axial direction.

16. A spinal construct comprising:
a rod;
a sleeve including a follower and a spring disposed thereabout, the rod being movably disposed in the sleeve, the follower being connected to the rod by a pin that extends through the follower and the rod, the spring applying a force to the follower such that the follower translates the rod relative to the sleeve in a first axial direction; and
a lock spring engageable with a lock disposed with the sleeve, the lock comprising a sheath and a flange fixed to the sheath, the lock spring comprising a first end directly engaging the flange and an opposite second end directly engaging an end wall of the sleeve, the lock being connected with the rod to resist and/or prevent translation of the rod relative to the sleeve in a second axial direction,
wherein the flange is configured to engage the end wall to prevent translation of the longitudinal element relative to the body in the first axial direction, and
wherein the body includes a stop facing the end wall, the flange being configured to engage the stop to prevent translation of the longitudinal element relative to the body in the second axial direction.

17. A spinal construct as recited in claim 16, wherein the sleeve includes an inner surface having a tapered portion, the sheath comprising a plurality of openings and a bearing disposed each of the openings, the bearings being configured to slide between an outer surface of the rod and the tapered portion to crimp the rod with the tapered portion to resist and/or prevent translation of the longitudinal element relative to the body in the second axial direction.

18. A spinal construct as recited in claim 16, wherein the sleeve includes a groove and a ring disposed in the groove, the lock including a range of movement and the ring defining a limit to facilitate limitation of translation of the rod in the axial second direction.

* * * * *